(12) United States Patent
Tadepalli et al.

(10) Patent No.: US 11,021,421 B2
(45) Date of Patent: Jun. 1, 2021

(54) PREPARING UNSATURATED CARBOCYCLIC COMPOUNDS

(71) Applicants: INTERNATIONAL FLAVORS & FRAGRANCES INC., New York, NY (US); Rutgers, The State University of New Jersey, Piscataway, NJ (US)

(72) Inventors: Sunitha Rao Tadepalli, Morganville, NJ (US); Alan Stuart Goldman, Highland Park, NJ (US); Xiaoguang Zhou, Highland Park, NJ (US); Geatesh Karunakaran Tampy, Colts Neck, NJ (US); John Cherkauskas, Burlington, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 157 days.

(21) Appl. No.: 15/843,810

(22) Filed: Dec. 15, 2017

(65) Prior Publication Data

US 2018/0362420 A1 Dec. 20, 2018

Related U.S. Application Data

(63) Continuation-in-part of application No. 15/624,749, filed on Jun. 16, 2017, now Pat. No. 10,435,345.

(60) Provisional application No. 62/351,062, filed on Jun. 16, 2016.

(51) Int. Cl.
| | |
|---|---|
| *C07C 5/42* | (2006.01) |
| *C07C 5/50* | (2006.01) |
| *C07C 5/333* | (2006.01) |
| *C07C 5/367* | (2006.01) |

(52) U.S. Cl.
CPC .............. *C07C 5/50* (2013.01); *C07C 5/3337* (2013.01); *C07C 5/367* (2013.01); *C07C 2523/46* (2013.01); *C07C 2531/24* (2013.01); *C07C 2602/08* (2017.05); *C07C 2602/10* (2017.05); *C07C 2602/24* (2017.05); *C07C 2602/26* (2017.05); *C07C 2602/28* (2017.05)

(58) Field of Classification Search
CPC .......... C07C 5/50; C07C 5/42; C07C 2523/46
See application file for complete search history.

(56) References Cited

U.S. PATENT DOCUMENTS

| | | | | |
|---|---|---|---|---|
| 3,751,500 | A * | 8/1973 | Hall ...................... | C11B 9/0049 585/22 |
| 10,435,345 | B2 * | 10/2019 | Tadepalli ................ | C07C 45/66 |
| 2019/0389791 | A1 * | 12/2019 | Tadepalli .............. | C07C 67/317 |

OTHER PUBLICATIONS

Adkins, H., et al. "Catalytic Dehydrogenation of Hydroaromatic Compounds in Benzene. III. Compounds Containing Gen Dialkyl Groups." J. Am. Chem. Soc. (1949), vol. 71, pp. 2958-2961. (Year: 1949).*
Choi, J., et al. "Dehydrogenation and Related Reactions Catalyzed by Iridium Pincer Complexes." Chem. Rev. (2011), vol. 111, pp. 1761-1779. (Year: 2011).*
Gupta, M., et al. "Catalytic Dehydrogenation of Cycloalkanes to Arenes by a Dihydrido Iridium P—C—P Pincer Complex." J. Am. Chem. Soc. (1997), vol. 119, pp. 840-841. (Year: 1997).*
Adkins, H., et al. "Catalytic Dehydrogenation of Hydroaromatic Compounds in Benzene. III. Compounds Containing Gem Dialkyl Groups." J. Am. Chem. Soc. (1949), vol. 71, pp. 2958-2961. (Year: 1949).*
Choi, J., et al. "Dehydrogenation and Related Reactions Catalyzed by Iridium Pincer Complexes." Chem. Rev. (2011), vol. 111, pp. 1761-1779. (Year: 2011).*

* cited by examiner

*Primary Examiner* — John S Kenyon

(57) ABSTRACT

Disclosed are methods of preparing unsaturated carbocyclic compounds through dehydrogenation of corresponding saturated carbocyclic compounds.

24 Claims, 15 Drawing Sheets

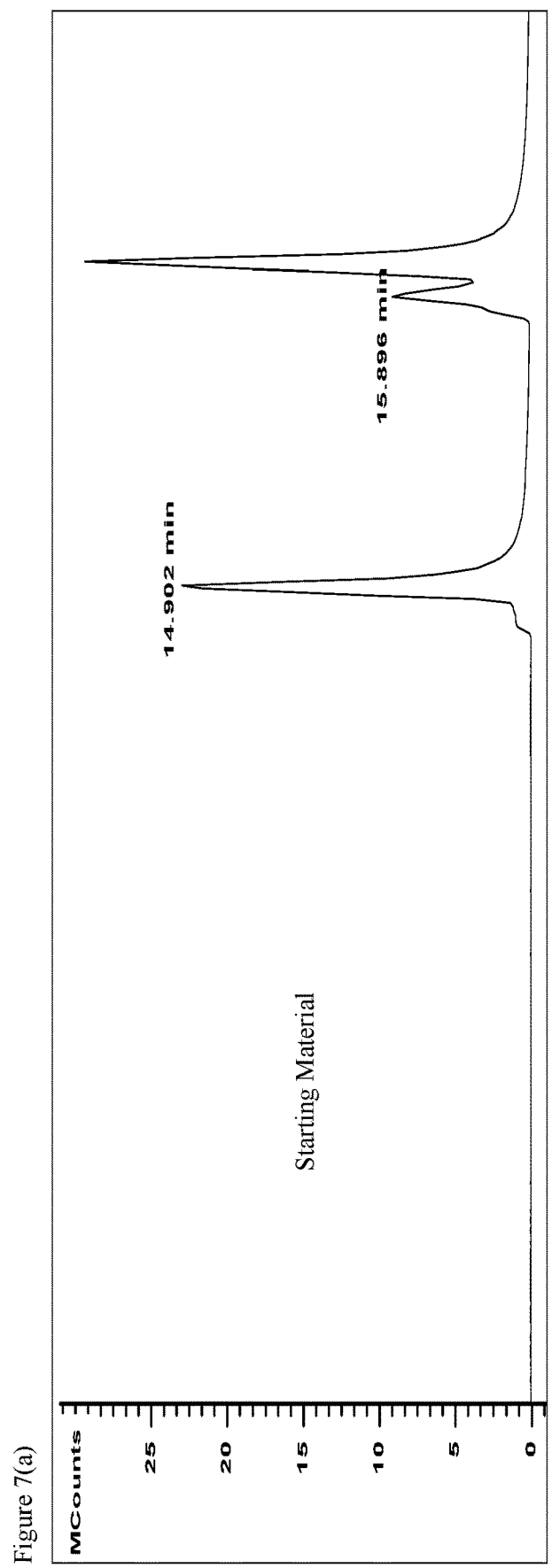

PREPARING UNSATURATED CARBOCYCLIC COMPOUNDS

CROSS-REFERENCE TO A RELATED APPLICATION

This application claims priority to U.S. application Ser. No. 15/624,749 filed on Jun. 16, 2017, which claims priority to U.S. Application, Ser. No. 62/351,062, filed on Jun. 16, 2016. The contents of both applications are incorporated herein by reference in entirety.

FIELD OF THE INVENTION

This application relates to methods of preparing unsaturated compounds, especially unsaturated carbocyclic compounds useful in the fragrance industry, through dehydrogenation of saturated compounds using Pincer catalyst.

BACKGROUND OF THE INVENTION

Olefins (alkenes) are versatile raw materials in organic synthesis, polymerization, and chemical processes, but they are not as widely available naturally as alkanes. Given the abundance of saturated hydrocarbon or alkanes in nature, dehydrogenation of alkanes provides a sustainable production of alkenes. This approach eliminates significant amount of waste generated from alternate multi-step chemical methods that are used to produce these olefins.

Different dehydrogenation methods have been developed. Traditional methods involve use of stoichiometric amounts of halogenated reagents and/or precious metals thus generating a lot of waste. Alternate one-step catalytic methods have been developed, but productivity and selectivity remains to be an issue especially when multiple regio-isomers can be formed in the dehydrogenation process. Especially in the case of higher alkanes, low selectivity and conversion often severely limit the utility of dehydrogenation.

Accordingly, there remains a need for green dehydrogenation methods that can produce high yield and great selectivity via engineering and catalytic methods.

SUMMARY OF THE INVENTION

Many fragrance intermediates and ingredients contain unsaturated backbones usually including mono- or multi-carbocyclic rings with or without functional groups. Dehydrogenation from the corresponding saturated compounds to yield these unsaturated compounds often encounters low-selectivity issues, giving rise to different regio-isomers of olefins or the aromatic counterparts. It has been unexpectedly discovered that pincer-iridium catalysts are efficient to tackle this challenge.

Accordingly, one aspect of this invention relates to preparation of an unsaturated carbocyclic compound through selective dehydrogenation of a corresponding saturated carbocyclic compound using a pincer-iridium catalyst.

The term "unsaturated carbocyclic compound" refers to compounds of Formula (II) below. The term "corresponding saturated compound" refers to compounds of Formula (I) below.

Other aspects or benefits of the present invention will be reflected in the following drawings, detailed description, and claims.

BRIEF DESCRIPTION OF FIGURES

FIG. 7(a) shows the GC-MS chromatogram of 1,1,2,3,3-pentamethylhexahydro-indane, the starting material used in the reaction of Example 7.

DETAILED DESCRIPTION OF THE INVENTION

Figure 1A:
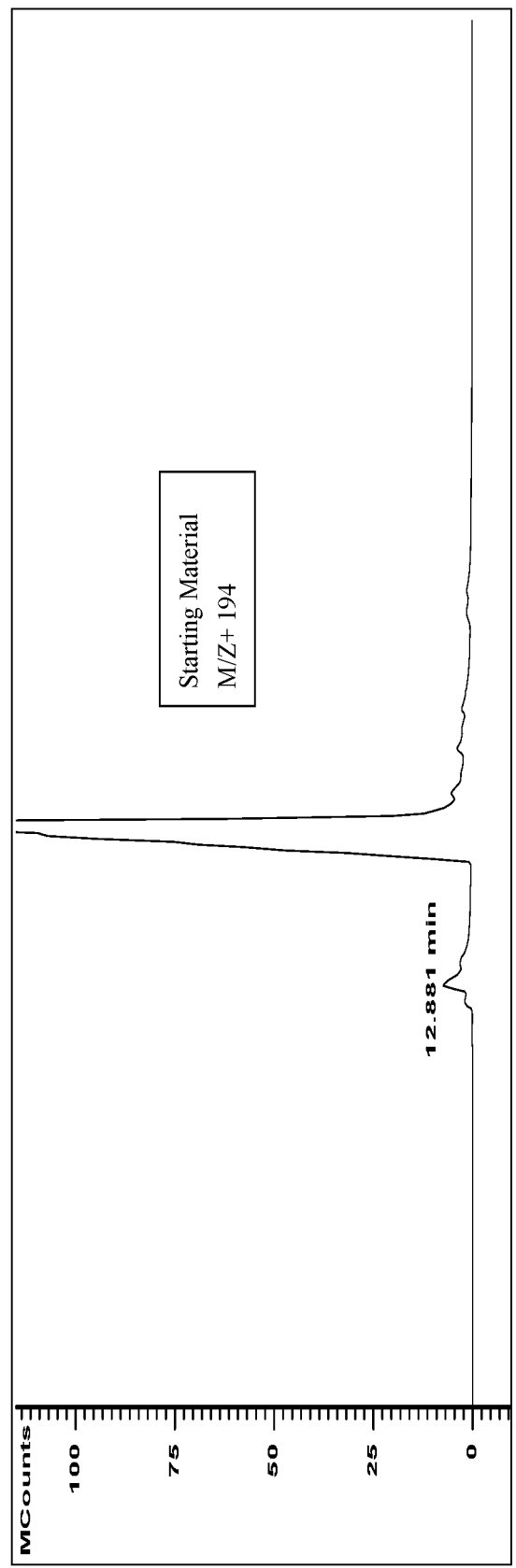
FIG. 1(a) shows the GC-MS chromatogram of 1,1,4,4-tetramethyl-decalin, the starting material used in the reactions of Examples 1-4.

In one aspect, the present invention provides a method of preparing an unsaturated compound, comprising dehydrogenation of a corresponding saturated compound in the presence of a pincer-iridium catalyst under conditions that effect loss of one or more molecules of hydrogen ($H_2$) per molecule of the saturated compound.

The saturated compounds are represented by Formula (I) below:

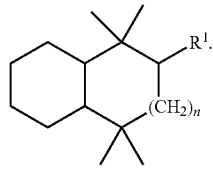

Formula (I)

In this formula, $R^1$ is H or $CH_3$ and n is 0 or 1.

The structures of two representative compounds of Formula (I) are shown below:

Compound 1

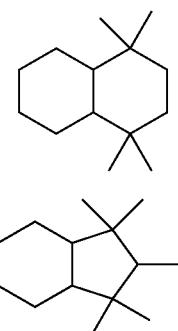

Compound 2

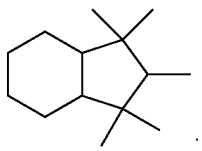

The dehydrogenation of the compounds of Formula (I) forms the unsaturated compounds of Formula (II):

Formula (II)

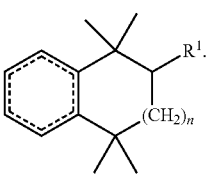

$R^1$ and n are defined above. Each --- represents a double bond, and the number of the double bonds represented by --- is 1, 2 or 3.

Representative products derived from Compound 1 include Compound 3 and analogs (e.g., Compounds 3a-c), Compound 4 and analogs (e.g., Compounds 4a-e), Compound 5, and any combination thereof:

Compound 3

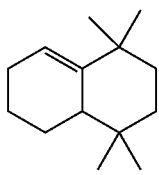

Compound 4

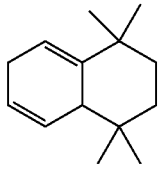

Compound 5

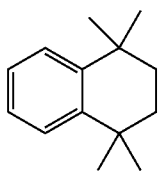

Compound 3a

Compound 3b

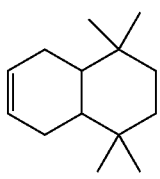

Compound 3c

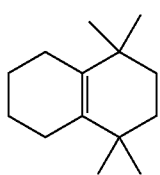

Compound 4a

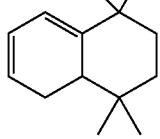

Compound 4b

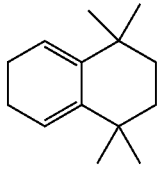

Compound 4c

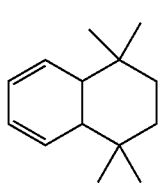

Compound 4d

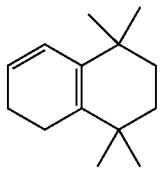

Compound 4e

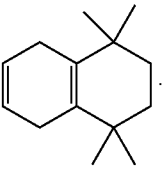

Representative products prepared from Compound 2 include Compound 6 and analogs, Compound 7 and analogs (e.g., Compounds 9-11), Compound 8, and any combination thereof:

Compound 6

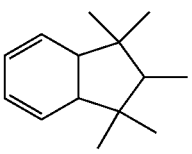

-continued

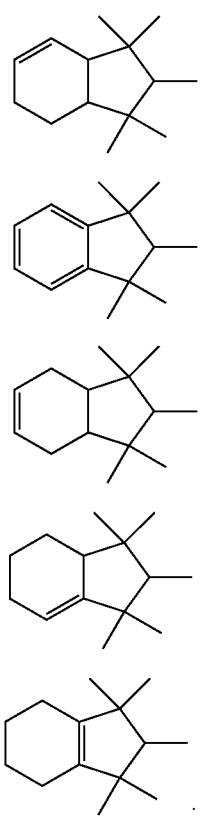

Compound 7

Compound 8

Compound 9

Compound 10

Compound 11

A pincer-iridium catalyst is a catalyst having an iridium atom and a pincer ligand that binds tightly to three adjacent coplanar sites on iridium in a meridional configuration. It is used in the amount of 0.1 to 50% (e.g., 0.5 to 20%, 1 to 10%, and 2 to 8%) by mole of the compound of Formula (I).

Exemplary pincer-iridium catalysts include ($iPr_4$PCOP)Ir($C_2H_4$), ($iPr_4$PCP)Ir($C_2H_4$), ($iPr_4$POCOP)Ir($C_2H_4$), ($tBu_4$POCOP)Ir$H_n$ (n is 1, 2, 3, or 4, preferably n is 2 or 4.), ($tBu_4$PCP)Ir$H_n$ (n is 1, 2, 3, or 4, preferably n is 2 or 4.), and any combinations thereof.

The pincer-iridium catalyst ($iPr_4$PCOP)Ir($C_2H_4$) has the following structure:

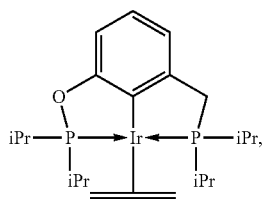

in which iPr represents isopropyl.

In one embodiment, the conditions include one or more solvents (e.g., xylene, acetic acid, toluene, ethyl acetate, DMSO, and DMF), an elevated temperature (e.g., at least 50° C., at least 100° C., 50-800° C., 100-800° C., 100-400° C., and 150-350° C.), and/or a stream of nitrogen to purge liberated hydrogen. In another embodiment, the conditions include one or more hydrogen acceptor (e.g., tertiary butyl ethylene, 3,3-dimethylbut-1-ene, cyclohexene and other alkenes) to consume the liberated hydrogen.

The duration of the dehydrogenation reaction varies from 30 minutes to 120 hours (e.g., 30 minutes to 60 hours, 1 to 30 hours, and 1 to 12 hours), depending on the solvent, reaction temperature, the starting material, the catalyst and its concentration, etc.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The invention is described in greater detail by the following non-limiting examples. Without further elaboration, it is believed that one skilled in the art can, based on the description herein, utilize the present invention to its fullest extent. All publications cited herein are incorporated by reference in their entirety.

EXAMPLES

All the reagents used in the examples below were degassed and dried. The reagents include starting materials, catalysts, solvents, and hydrogen receptors.

Example 1: Selective Dehydrogenation of Compound 1 Using a Pincer-Iridium Catalyst

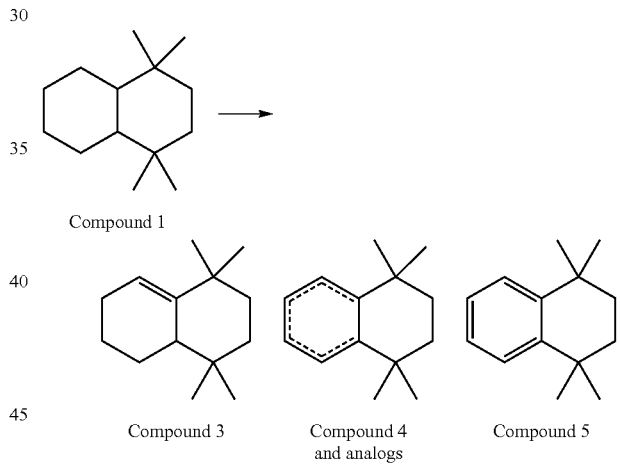

Compound 1

Compound 3   Compound 4   Compound 5
             and analogs

------ represents a double bond,
and the number of double bond is 2

Figure 1B:
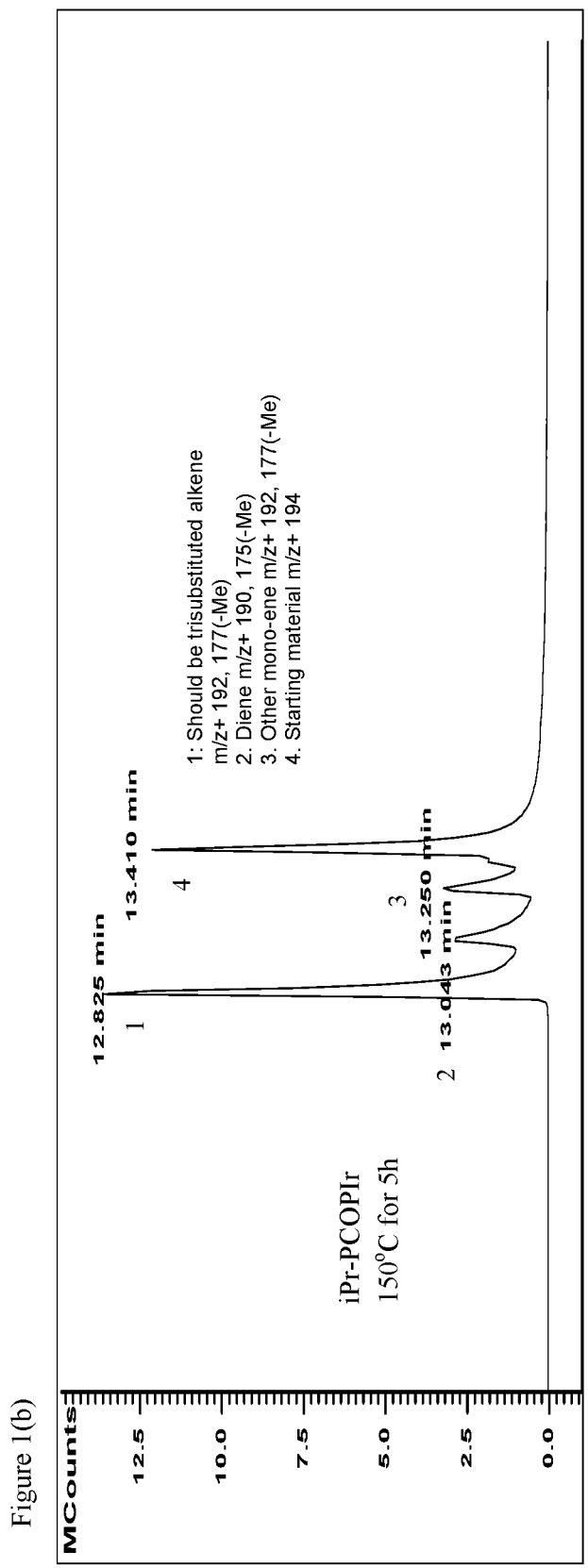
FIG. 1(b) shows the GC-MS chromatogram of the reaction mixture of Example 1.
Figure 1C:
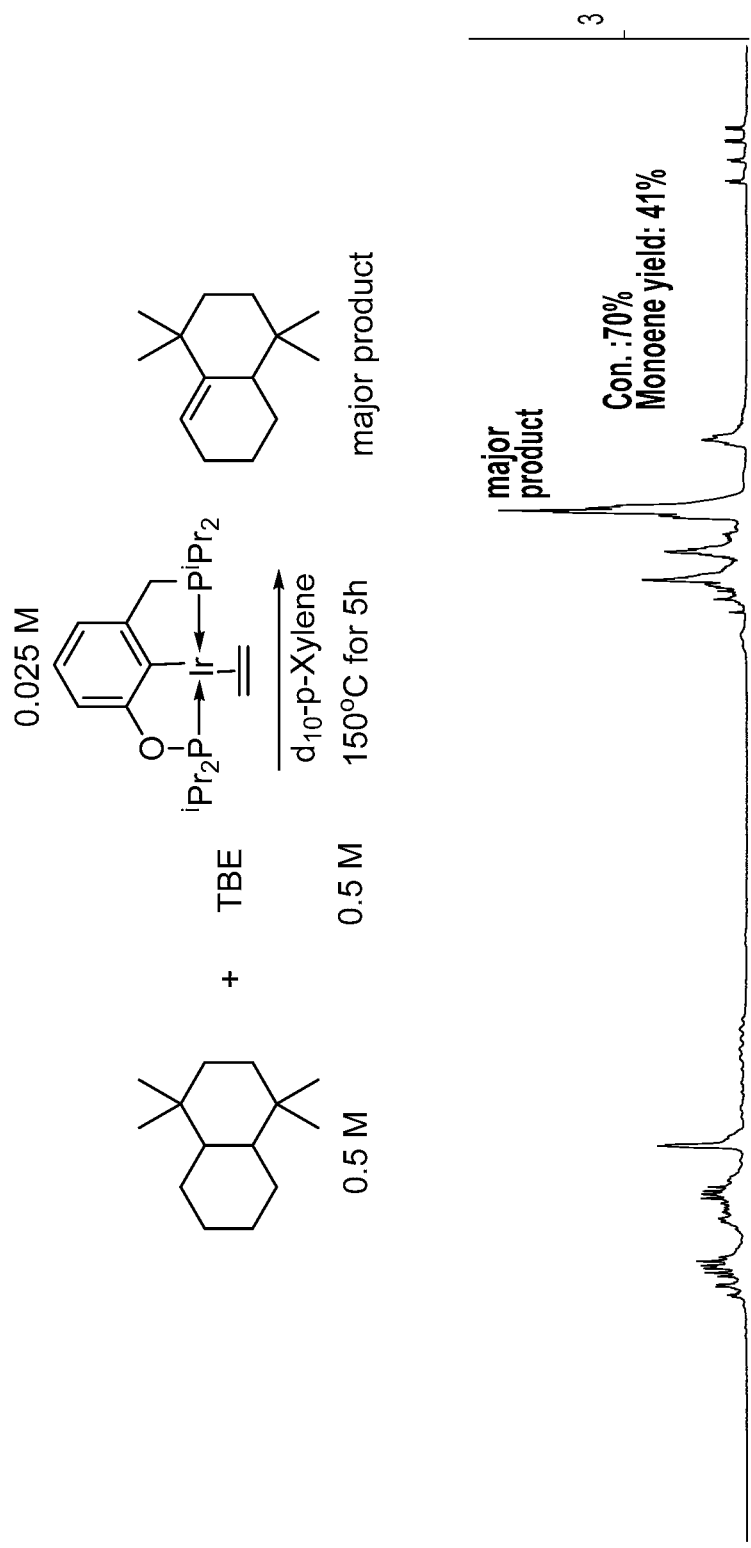
FIG. 1(c) shows the NMR chromatogram of the reaction mixture of Example 1.

In a J-Young tube were added in sequence the following agents: (i) a Pincer-iridium catalyst, i.e., 5.6 mg of ($iPr_4$PCOP)Ir($C_2H_4$) (5% by mole of the saturated compound of Formula (I) as described below, 0.01 mmol at a concentration of 0.025 M in the resultant reaction mixture), (ii) a saturated compound of Formula (I), i.e., 38.8 mg of 1,1,4,4-tetramethyl-decalin (1 equivalent, 0.2 mmol, 0.5 M), and (iii) a hydrogen acceptor, i.e., 16.8 mg of tertiary butyl ethylene ("TBE", 1 equivalent, 0.2 mol, 0.5 M), followed by the addition of a deuterated solvent, i.e., 0.4 mL of p-xylene-$d_{10}$. The J-Young tube was sealed under argon and heated to 150° C. The reaction was monitored by GC-MS and $^1$H NMR. See FIGS. 1(a)-(c). After 5 hours, 1,1,4,4-tetramethyl-decalin was reacted at a conversion of 70%. A compound of Formula (II), i.e., Compound 3, was obtained at a yield of 41%. Both the conversion and yield was calculated using the GC-MS and $^1$H NMR data. The conversion was calculated as: the mass (by mole) of the saturated compound of Formula (I) consumed in the reaction/the mass (by mole) of the saturated compound added to the reaction×100%. The yield was calculated as: the actual yield (by mole) of the unsaturated compound of Formula (II)/the theoretical yield of the unsaturated compound of Formula (II)×100%.

Example 2

Figure 2A:
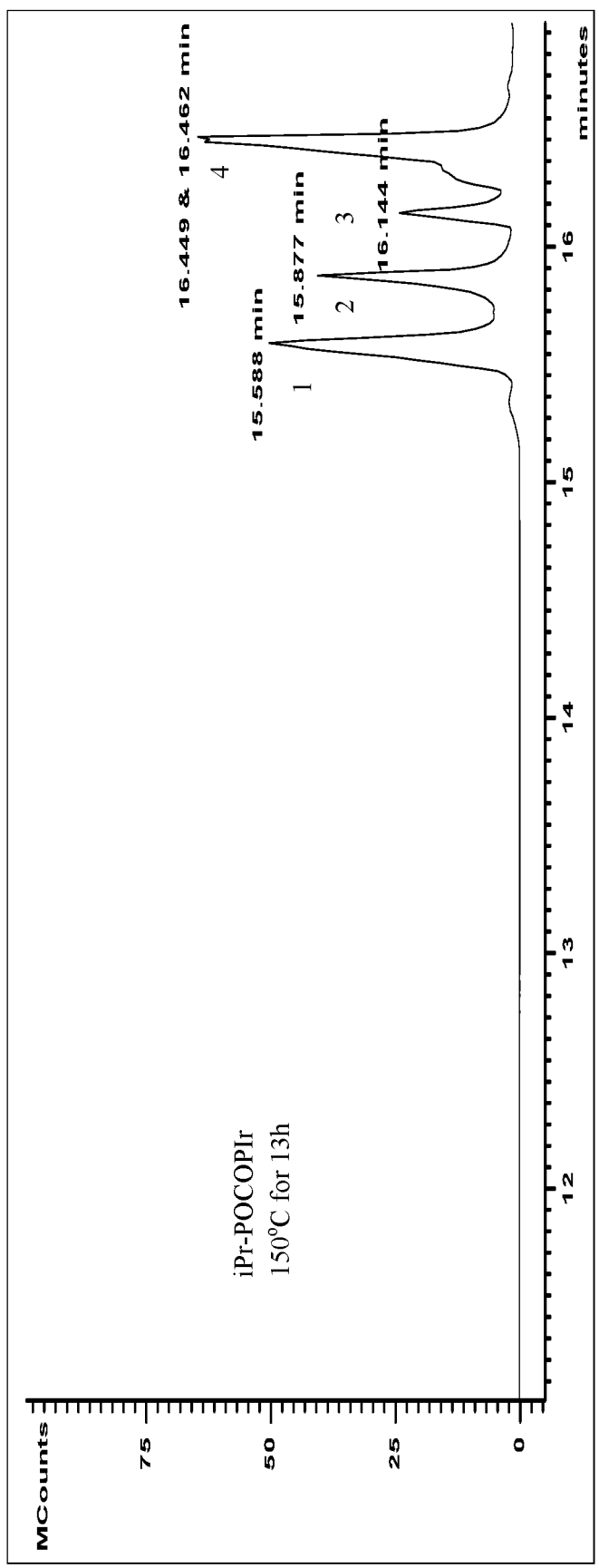
FIG. 2(a) shows the GC-MS chromatogram of the reaction mixture of Example 2.
Figure 2B:
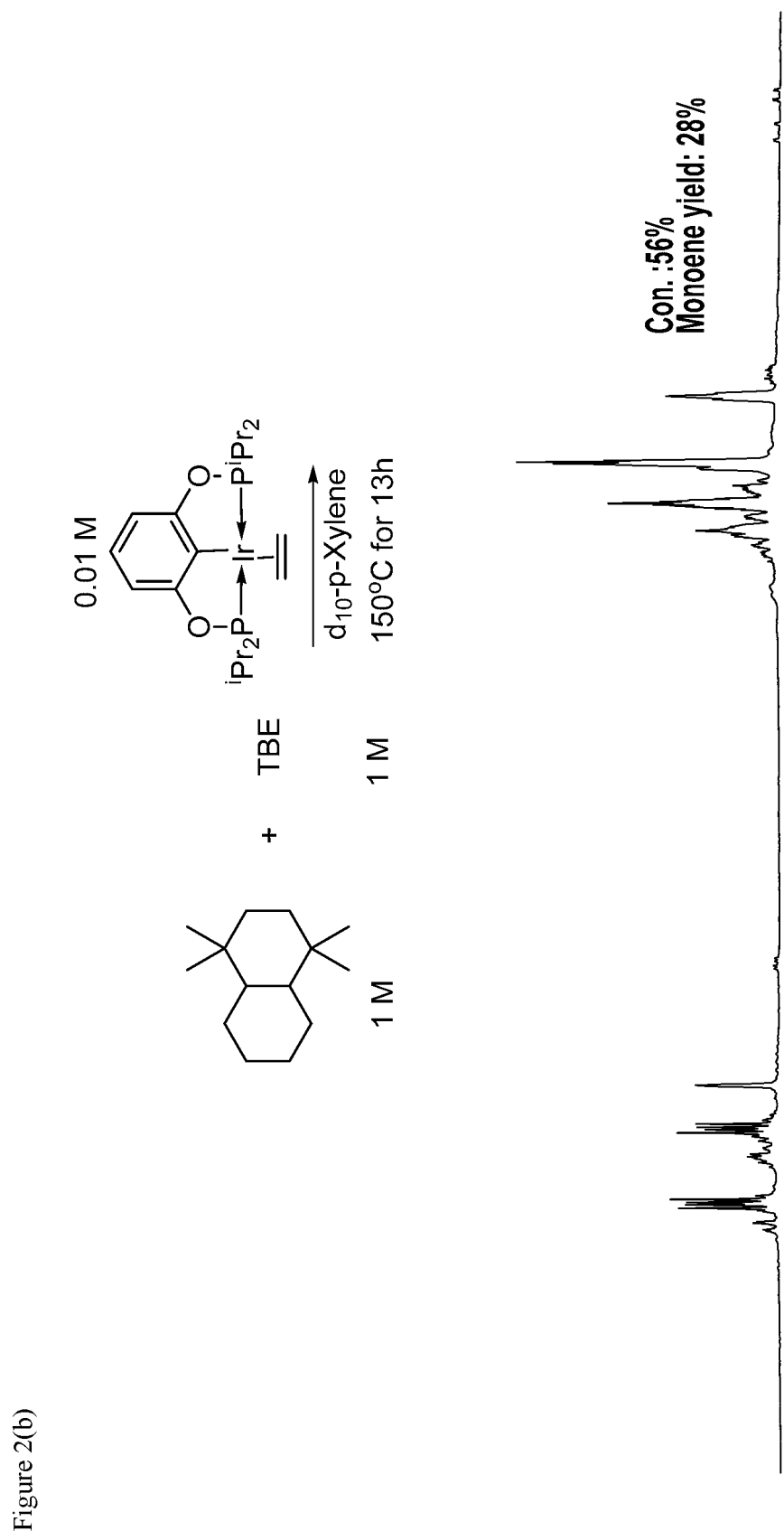
FIG. 2(b) shows the NMR chromatogram of the reaction mixture of Example 2.

In a J-Young tube were added 2.8 mg of Pincer-iridium catalyst (iPr$_4$POCOP)Ir(C$_2$H$_4$) (1 mol %, 0.005 mmol, 0.01 M), 97 mg of 1,1,4,4-tetramethyl-decalin (1 eq., 0.5 mmol, 1 M), and 42 mg of TBE (1 eq., 0.5 mol, 1 M), followed by the addition of 0.4 mL of p-xylene-d$_{10}$. The J-Young was sealed under argon and heated to 150° C. The reaction was monitored by GC-MS and $^1$H NMR. After 13 hours, 1,1,2,3,3-pentamethylhexahydro-indane was reacted at a conversion of 56% and Compound 3 was obtained at a yield of 28% as observed by GC-MS and 1H NMR. See FIGS. 2(a) and 2(b).

Example 3

Figure 3:
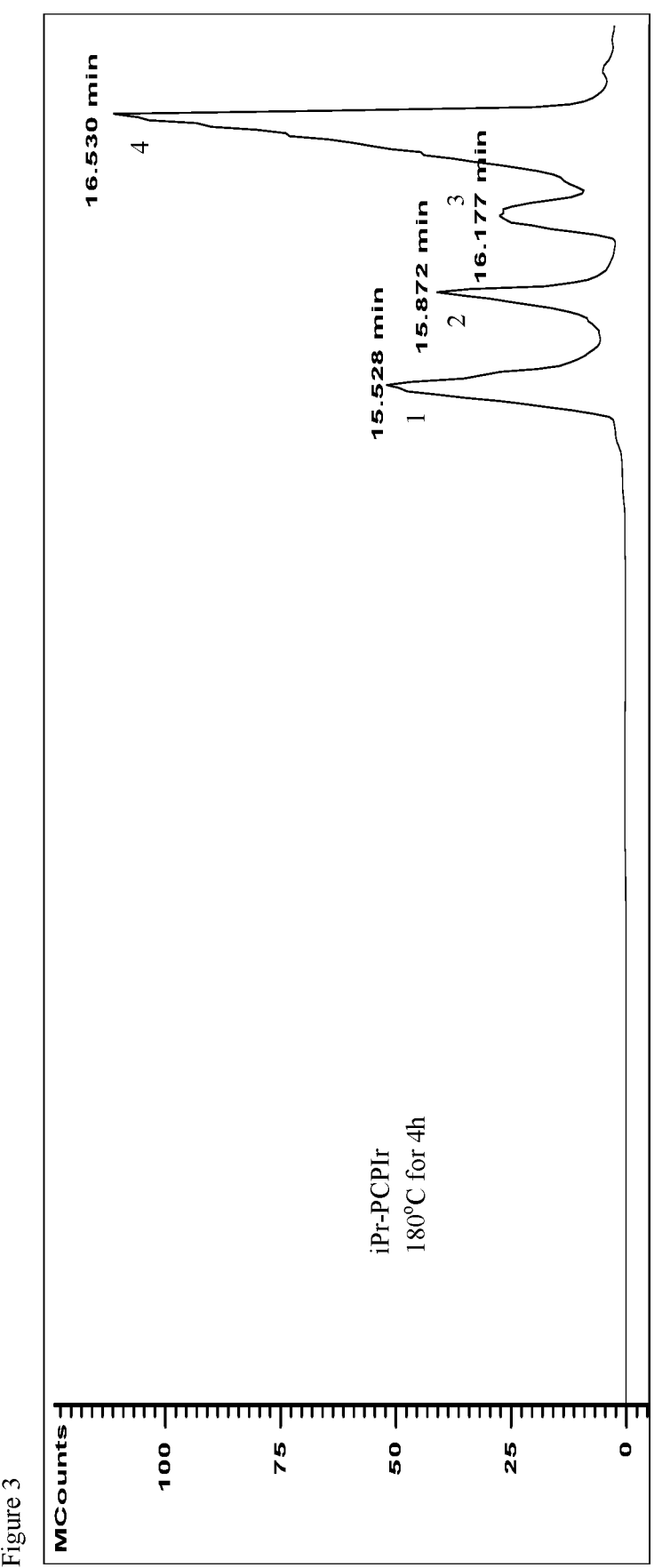
FIG. 3 shows the GC-MS chromatogram of the reaction mixture of Example 3.
Figure 4:
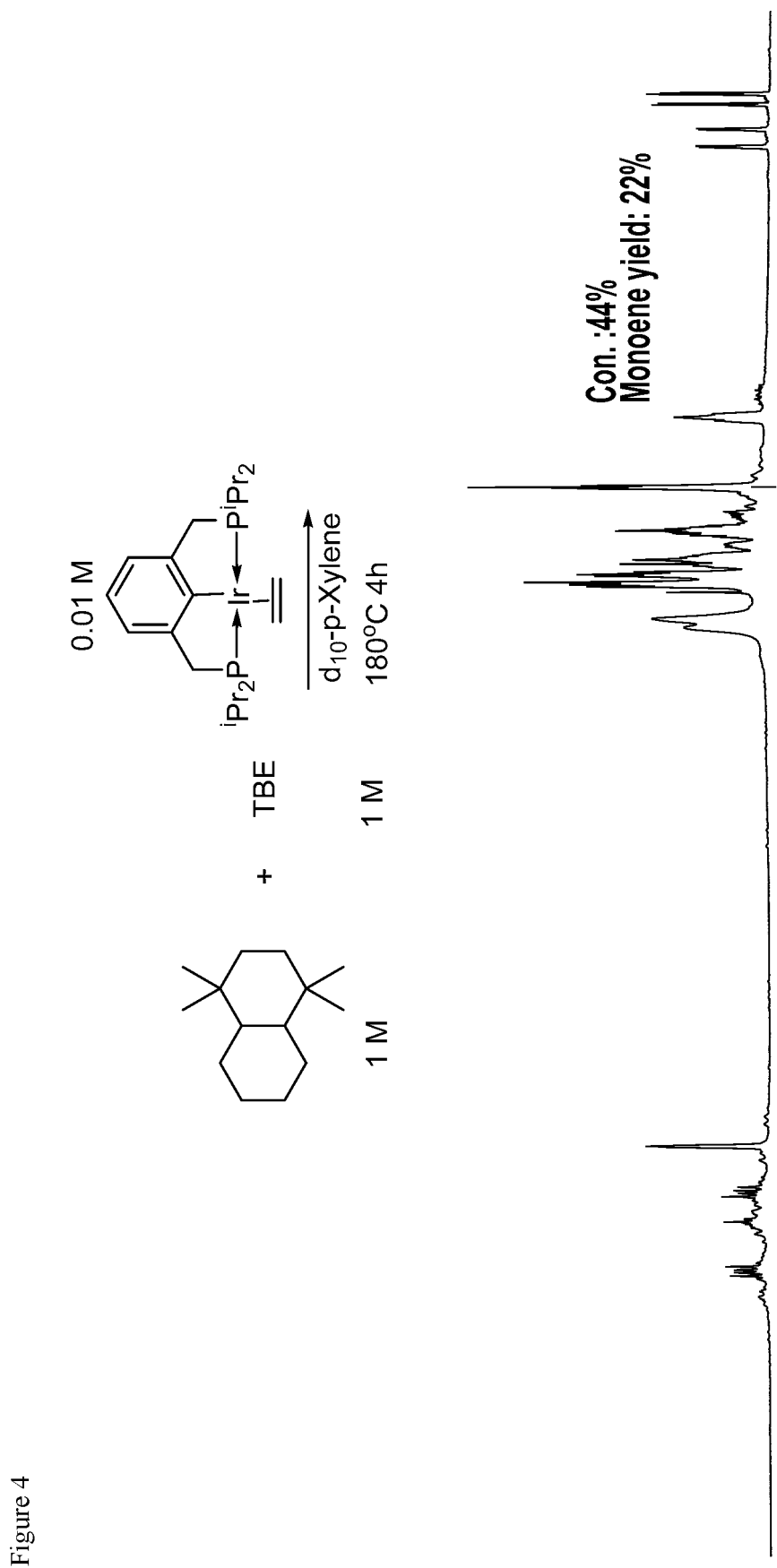
FIG. 4 shows the NMR chromatogram of the reaction mixture of Example 3.

The procedure in Example 2 was followed except that the reaction was carried out at 180° C., instead of 150° C. After heating for 4 hours, 1,1,2,3,3-pentamethylhexahydro-indane was reacted at a conversion of 44% and Compound 3 was obtained at a yield of 22% as observed by GC-MS and 1H NMR. See FIGS. 3 and 4.

Example 4

In a 600 mL autoclave were added (i) 9.97 g of (iPr$_4$PCOP)Ir(C$_2$H$_4$) (5 mol %, 0.0178 mol, 0.032 M), (ii) 69 g of 1,1,4,4-tetramethyl-decalin (1 eq., 0.356 mol, 0.65 M), and (iii) 40.4 g of TBE (1.35 eq., 0.481 mol, 0.87 M), followed by the addition of 400 mL of p-xylene. The autoclave was sealed under argon and heated to 155° C. The reaction was monitored by GC-MS. After 6.5 hours, 1,1,2,3,3-pentamethylhexahydro-indane was reacted at a conversion of 95% and Compound 3 was obtained at a yield of 50% as observed by GC-MS.

Example 5: Selective Dehydrogenation of Compound 2 Using a Pincer-Iridium Catalyst

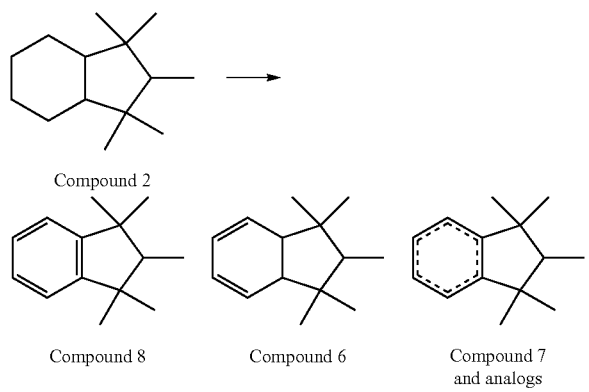

------ represents a double bond, the number of double bond is 1.

Figure 5A:
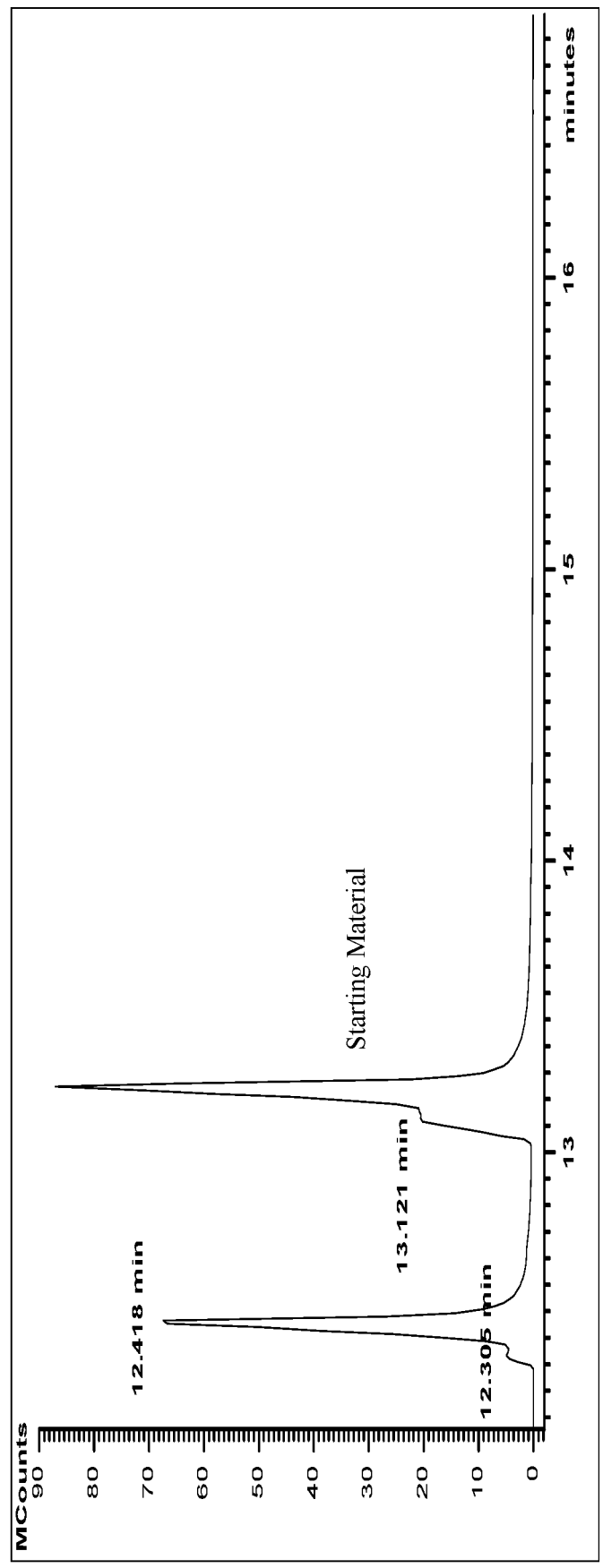
FIG. 5(a) shows the GC-MS chromatogram of 1,1,2,3,3-pentamethylhexahydro-indane, the starting material used in the reactions of Examples 5 and 6.
Figure 5B:
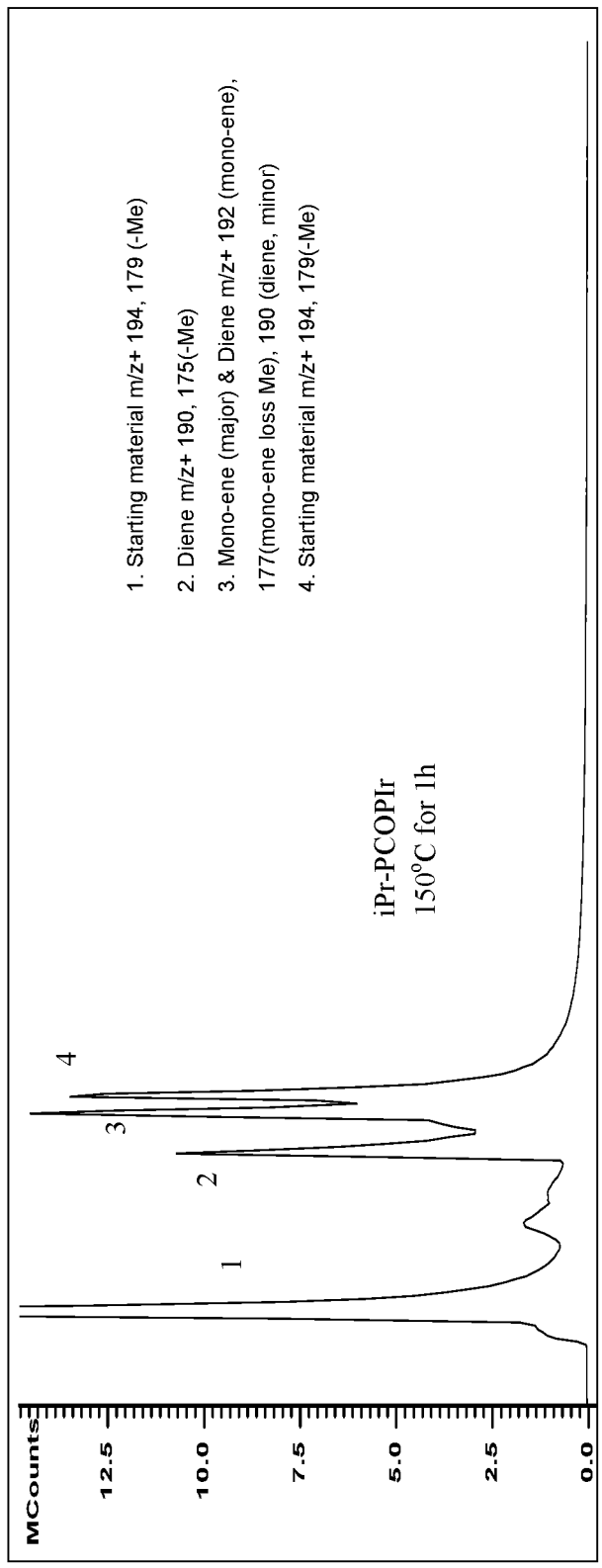
FIG. 5(b) shows the GC-MS chromatogram of the reaction mixture of Example 5.
Figure 5C:
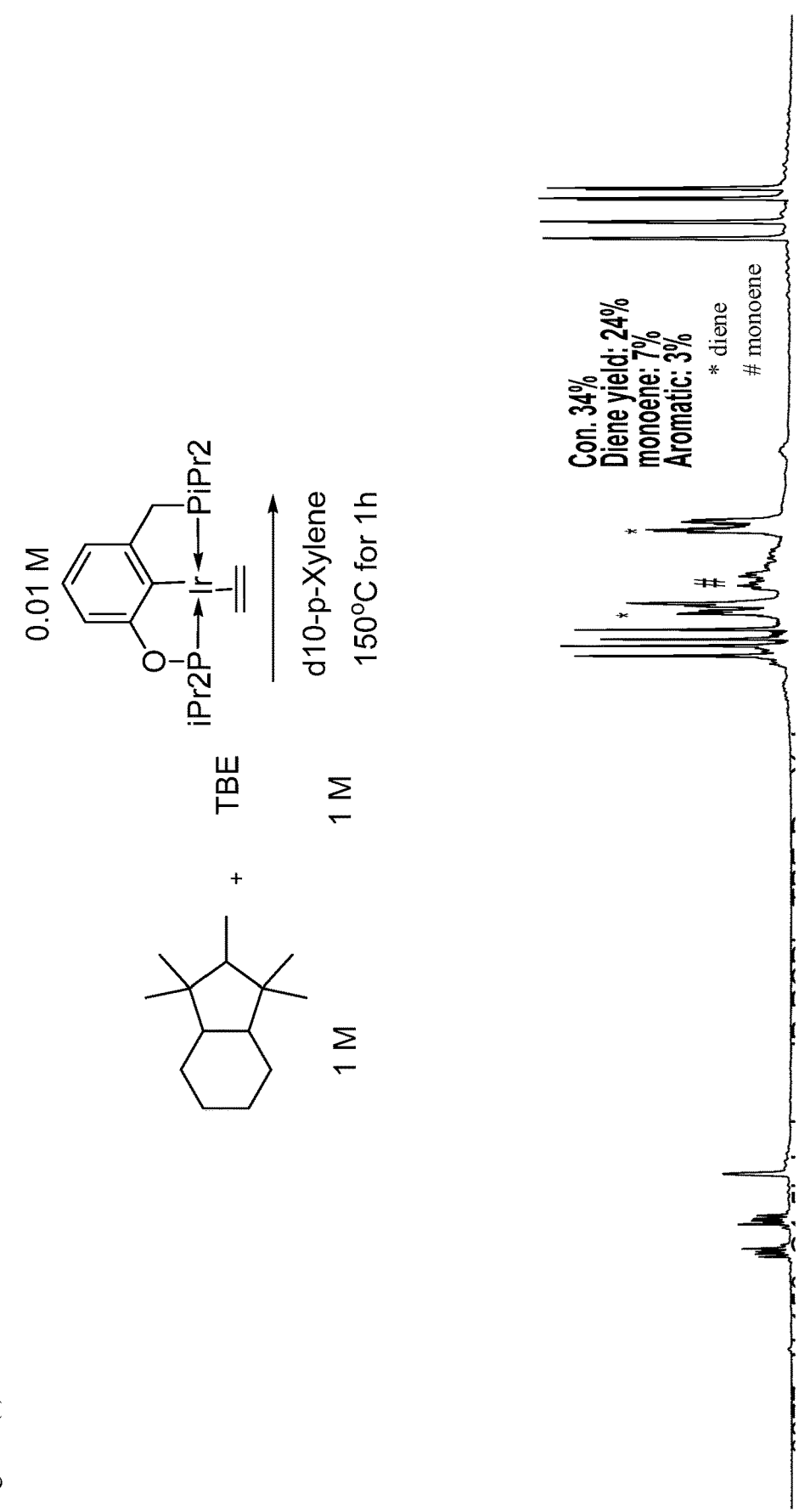
FIG. 5(c) shows the NMR chromatogram of the reaction mixture of Example 5.

In a J-Young tube were added (i) 2.8 mg of the Pincer-iridium catalyst (iPr$_4$PCOP)Ir(C$_2$H$_4$) (1 mol %, 0.005 mmol, 0.01 M), (ii) a compound of Formula (I), i.e., 97 mg of 1,1,2,3,3-pentamethylhexahydro-indane (1 eq., 0.5 mmol, 1 M), and (iii) 42 mg TBE (1 eq., 0.5 mol, 1 M), followed by 0.4 mL of p-xylene-d$_{10}$. The J-Young was sealed under argon and heated to 150° C. The reaction was monitored by GC-MS and $^1$H NMR. See FIGS. 5(a)-(c). After 1 hour, 1,1,2,3,3-pentamethylhexahydro-indane was reacted at a conversion of 34% and Compound 6 was obtained at a yield of 24% as observed by GC-MS and $^1$H NMR. The aromatic product will increase quickly if continue heating.

Example 6

Figure 6A:
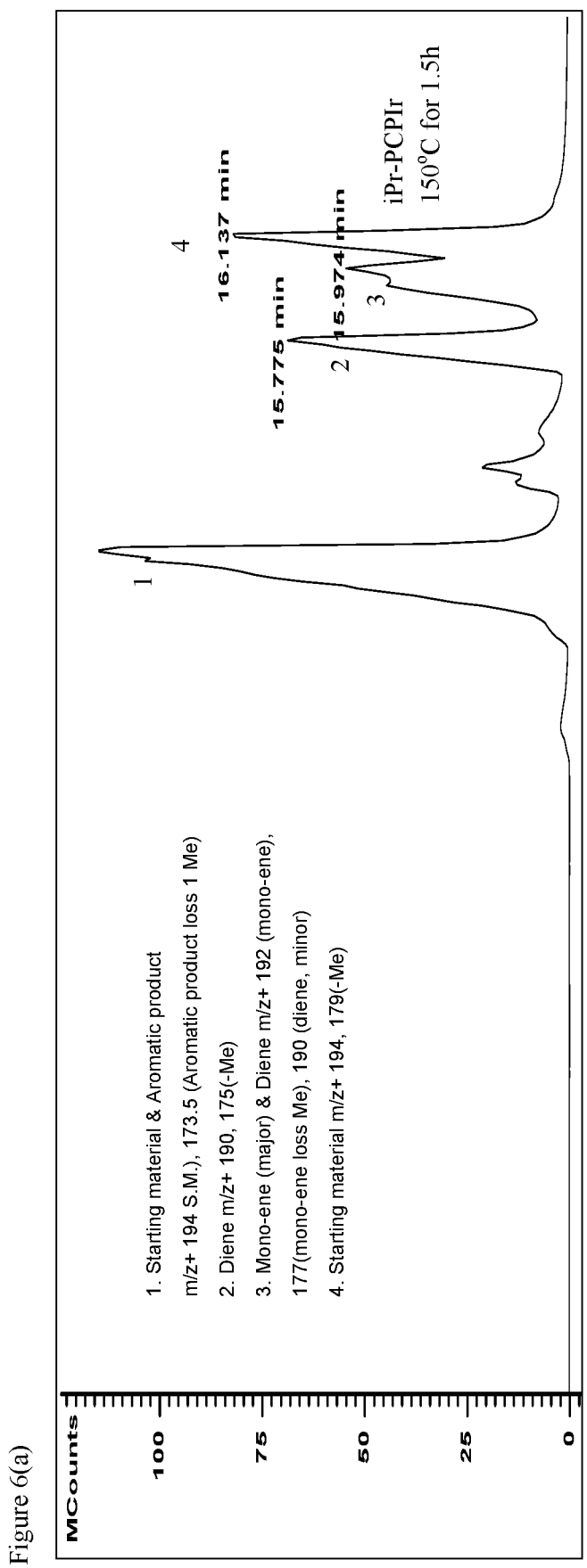
FIG. 6(a) shows the GC-MS chromatogram of the reaction mixture of Example 6.
Figure 6B:
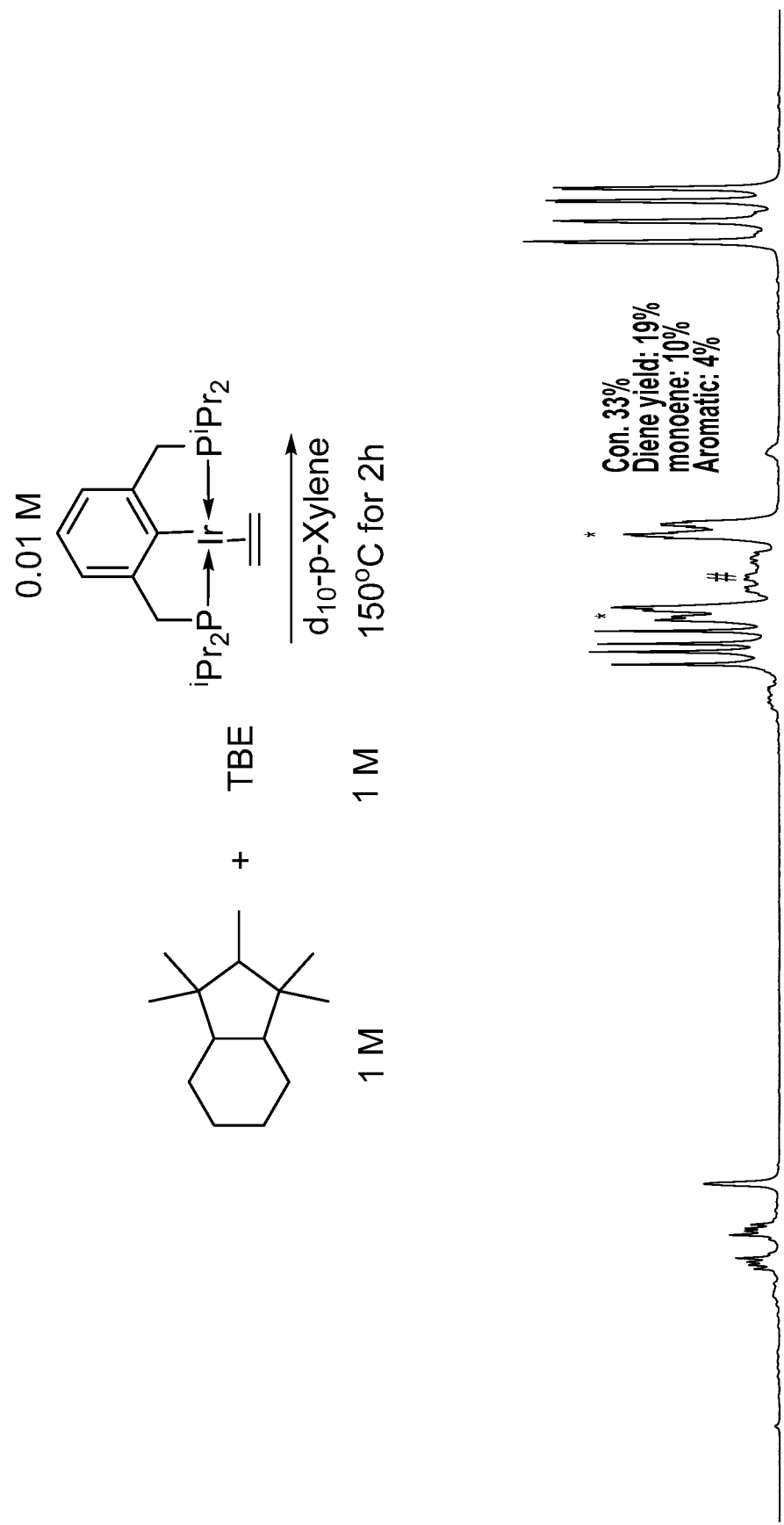
FIG. 6(b) shows the NMR chromatogram of the reaction mixture of Example 6.

The procedure described in Example 5 was followed except that (iPr$_4$PCP)Ir(C$_2$H$_4$) was used, instead of (iPr$_4$PCOP)Ir(C$_2$H$_4$). After 2 hours, 1,1,2,3,3-pentamethylhexahydro-indane was reacted at a conversion of 33% and Compound 6 was obtained at a yield of 19% as observed by GC-MS and $^1$H NMR. See FIGS. 6(a) and 6(b).

Example 7

Figure 7B:
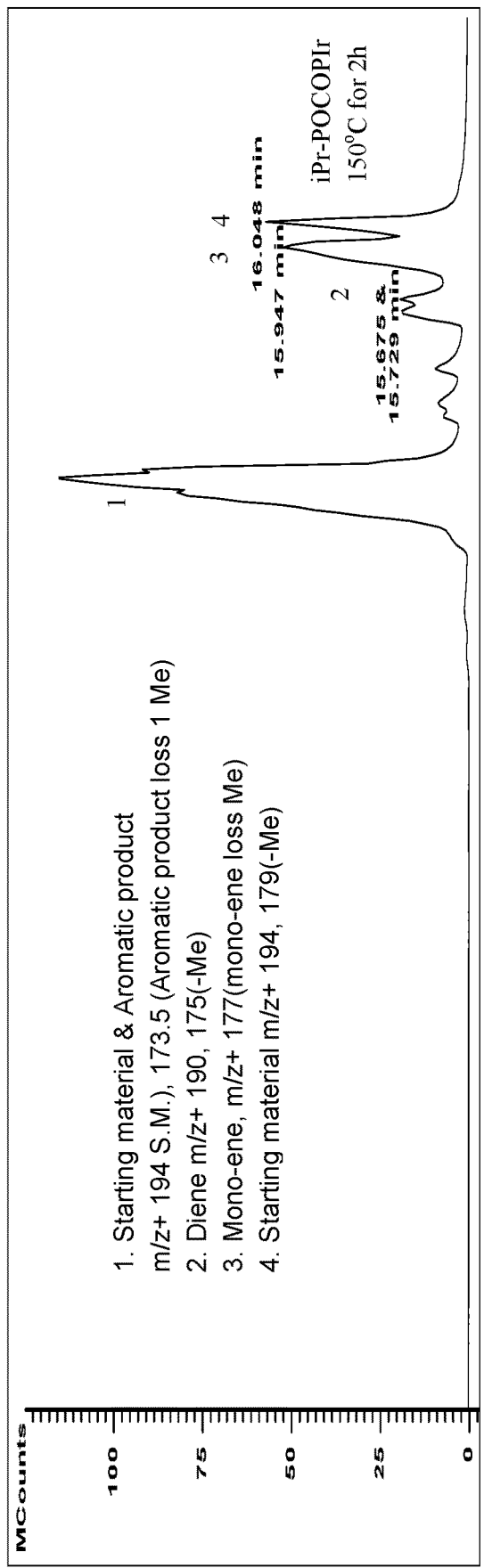
FIG. 7(b) shows the GC-MS chromatogram of the reaction mixture of Example 7.
Figure 7C:
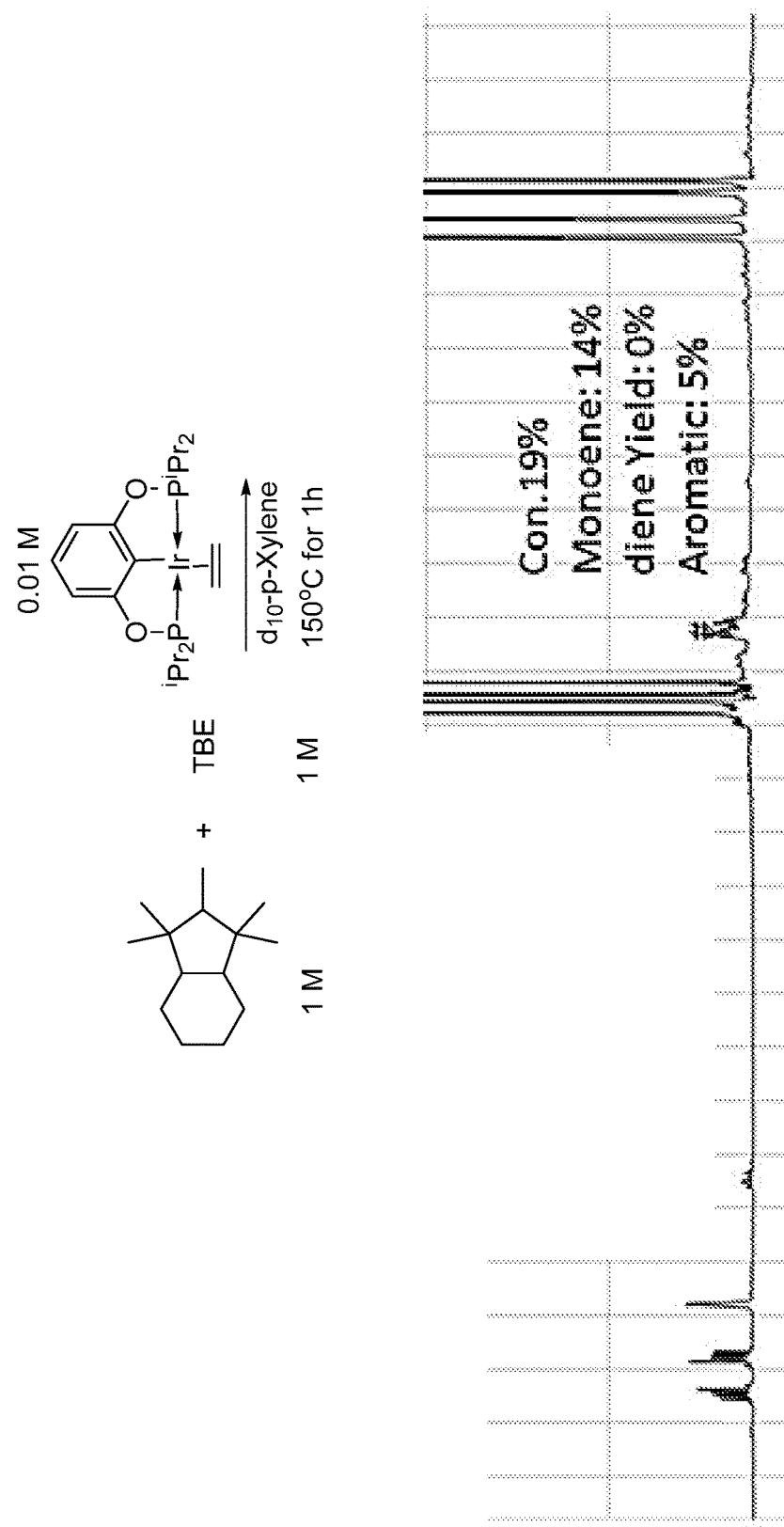
FIG. 7(c) shows the NMR chromatogram of the reaction mixture of Example 7.

The procedure described in Example 5 was followed except that (iPr$_4$POCOP)Ir(C$_2$H$_4$) was used, instead of (iPr$_4$PCP)Ir(C$_2$H$_4$). After 2 hours, 1,1,2,3,3-pentamethylhexahydro-indane was reacted at a conversion of 19% and Compound 7 and analogs were obtained at a yield of 14% as observed by GC-MS and $^1$H NMR. See FIGS. 7(a) and 7(b).

What is claimed is:

1. A method of preparing an unsaturated compound of Formula (II), comprising dehydrogenation of a saturated compound of Formula (I) in the presence of a pincer-iridium catalyst under conditions that effect loss of one or more molecules of hydrogen (H$_2$) per molecule of the saturated compound:

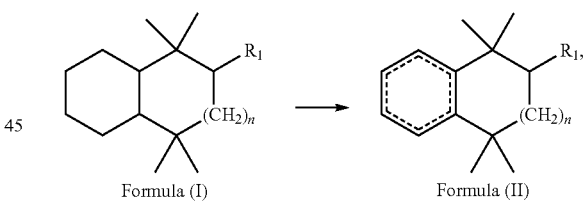

wherein R$_1$ is H or CH$_3$, n is 1, each --- represents a double bond, the number of the double bonds represented by --- in Formula (II) is 1 or 2, and said conditions comprise one or more solvents.

2. The method of claim 1, further comprising adding one or more hydrogen acceptors to the dehydrogenation reaction to consume the hydrogen molecules.

3. The method of claim 2, wherein the hydrogen acceptor is 3,3-dimethylbut-1-ene.

4. The method of claim 1, wherein said pincer-iridium catalyst is (iPr$_4$PCOP)Ir(C$_2$H$_4$), (iPr$_4$PCP)Ir(C$_2$H$_4$), (iPr$_4$POCOP)Ir(C$_2$H$_4$), or any combination thereof.

5. The method of claim 1, wherein R$_1$ is H.

6. The method of claim 5, further comprising adding one or more hydrogen acceptors to the dehydrogenation reaction to consume the hydrogen molecules, wherein the hydrogen acceptor is 3,3-dimethylbut-1-ene, and the pincer-iridium catalyst is (iPr$_4$PCOP)Ir(C$_2$H$_4$).

7. The method of claim 1, wherein the one or more solvents are p-xylene, and the pincer-iridium catalyst is present at a level of 1% to 10% by mole of the compound of Formula (I).

8. The method of claim 1, wherein the number of the double bonds represented by --- is 1.

9. The method of claim 1, wherein the number of the double bonds represented by --- is 2.

10. The method of claim 1, wherein the conditions further comprise an elevated temperature, a stream of nitrogen to purge liberated hydrogen, or a combination thereof.

11. The method of claim 1, wherein the one or more solvents are xylene.

12. The method of claim 1, wherein the pincer-iridium catalyst is present at a level of 1% to 10% by mole of the compound of Formula (I).

13. A method of preparing an unsaturated compound of Formula (II), comprising dehydrogenation of a saturated compound of Formula (I) in the presence of a pincer-iridium catalyst under conditions that effect loss of one or more molecules of hydrogen ($H_2$) per molecule of the saturated compound:

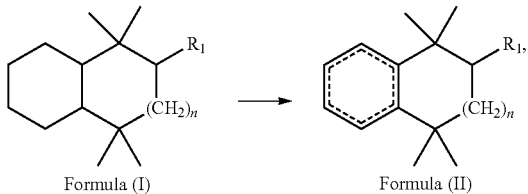

Formula (I)  Formula (II)

wherein $R_1$ is H or $CH_3$, n is 0 or 1, each --- represents a double bond, the number of the double bonds represented by --- in Formula (II) is 1 or 2, the pincer-iridium catalyst is present at a level of 1% to 10% by mole of the compound of Formula (I), and said conditions comprise one or more solvents.

14. The method of claim 13, further comprising adding one or more hydrogen acceptors to the dehydrogenation reaction to consume the hydrogen molecules.

15. The method of claim 14, wherein the hydrogen acceptor is 3,3-dimethylbut-1-ene.

16. The method of claim 13, wherein said pincer-iridium catalyst is ($iPr_4$PCOP)Ir($C_2H_4$), ($iPr_4$PCP)Ir($C_2H_4$), ($iPr_4$POCOP)Ir($C_2H_4$), or any combination thereof.

17. The method of claim 13, wherein $R_1$ is H and n is 1.

18. The method of claim 17, further comprising adding one or more hydrogen acceptors to the dehydrogenation reaction to consume the hydrogen molecules, wherein the hydrogen acceptor is 3,3-dimethylbut-1-ene, and the pincer-iridium catalyst is ($iPr_4$PCOP)Ir($C_2H_4$).

19. The method of claim 13, wherein $R_1$ is $CH_3$ and n is 0.

20. The method of claim 19, further comprising adding one or more hydrogen acceptors to the dehydrogenation reaction to consume the hydrogen molecules, wherein the hydrogen acceptor is 3,3-dimethylbut-1-ene, and the pincer-iridium catalyst is ($iPr_4$PCOP)Ir($C_2H_4$), ($iPr_4$PCP)Ir($C_2H_4$), ($iPr_4$POCOP)Ir($C_2H_4$), or any combination thereof.

21. The method of claim 13, wherein the one or more solvents are xylene.

22. The method of claim 13, wherein the number of the double bonds represented by --- is 1.

23. The method of claim 13, wherein the number of the double bonds represented by --- is 2.

24. The method of claim 13, wherein the conditions further comprise an elevated temperature, a stream of nitrogen to purge liberated hydrogen, or a combination thereof.

* * * * *